US011406754B2

(12) United States Patent
Streit et al.

(10) Patent No.: US 11,406,754 B2
(45) Date of Patent: Aug. 9, 2022

(54) PATCH PUMP (71) Applicant: TecMed AG, Burgdorf (CH)

(72) Inventors: Ursina Streit, Schoenbuehl (CH); Seline Staub, Winterthur (CH); Thomas Buri, Burgdorf (CH); Patrick Hostettler, Hasle (CH); Juerg Steck, Kirchberg (CH); Christophe Hofer, Burgdorf (CH); Andreas Koehli, Ipsach (CH); Florian Kuehni, Bern (CH); Marc Labudde, Spiegel (CH); Thomas Leuzinger, Muensingen (CH)

(73) Assignee: TECMED AG, Burgdorf (CH)

( * ) Notice: Subject to any disclaimer, the term of this patent is extended or adjusted under 35 U.S.C. 154(b) by 347 days.

(21) Appl. No.: 16/693,717

(22) Filed: Nov. 25, 2019

(65) Prior Publication Data
US 2020/0086044 A1    Mar. 19, 2020

Related U.S. Application Data

(63) Continuation of application No. PCT/IB2018/055271, filed on Jul. 17, 2018.

(30) Foreign Application Priority Data

Aug. 18, 2017 (EP) .................................. 17186867

(51) Int. Cl.
 *A61M 5/142* (2006.01)
(52) U.S. Cl.
 CPC ................... *A61M 5/14248* (2013.01); *A61M 2005/14252* (2013.01); *A61M 2005/14268* (2013.01);

(Continued)

(58) Field of Classification Search
 CPC .... A61M 5/14248; A61M 2005/14252; A61M 2005/14268
 See application file for complete search history.

(56) References Cited

U.S. PATENT DOCUMENTS 6,699,218 B2 *   3/2004   Flaherty ............ A61M 5/14248
                                                    604/131
6,749,587 B2 *   6/2004   Flaherty .................. A61P 25/04
                                                    604/151

(Continued)

FOREIGN PATENT DOCUMENTS

EP          2201657 B1      9/2016
WO       2007038060 A2      4/2007
WO       2009125398 A2     10/2009

OTHER PUBLICATIONS

International Preliminary Report on Patentability issued in International Application PCT/IB2018/055271, dated Feb. 27, 2020, 11 pages.

(Continued)

*Primary Examiner* — Laura A Bouchelle
(74) *Attorney, Agent, or Firm* — Dorsey & Whitney LLP

(57) ABSTRACT

A disposable module that can be coupled to a reusable module in order to form a pump for dispensing a medicament substance to a user in a metered manner in a coupled state, comprising a housing that encases the following components: a reservoir for receiving the substance to be dispensed; and at least one extensible cannula, which is fluidically connected to the reservoir either after being inserted or in a permanent manner. The disposable module may also comprise an electrical energy store, wherein the electrical energy necessary for the reusable module can be obtained both from the disposable module and also from a

(Continued)

A

B

C rechargeable battery in the reusable module, in order to ensure redundancy of the energy necessary for the reusable module.

20 Claims, 5 Drawing Sheets

(52) U.S. Cl.
CPC . *A61M 2205/35* (2013.01); *A61M 2205/8206* (2013.01); *A61M 2205/8256* (2013.01)

(56) References Cited

U.S. PATENT DOCUMENTS

| | | | | |
|---|---|---|---|---|
| 8,939,930 | B2 * | 1/2015 | Li | A61M 5/155 604/67 |
| 2003/0088238 | A1 * | 5/2003 | Poulsen | A61M 5/16827 604/890.1 |
| 2011/0054390 | A1 | 3/2011 | Searle et al. | |
| 2012/0184907 | A1 | 7/2012 | Smith et al. | |
| 2017/0354366 | A1 * | 12/2017 | Steensberg | A61P 3/08 |

OTHER PUBLICATIONS

International Search Report and Written Opinion with ISR translation issued for International Application No. PCT/IB2018/055271, dated Sep. 26, 2018, 19 pages.

\* cited by examiner

Fig. 4

PATCH PUMP

CROSS-REFERENCE TO RELATED APPLICATIONS

This application is a continuation of International Application No. PCT/IB2018/055271 filed Jul. 17, 2018, which claims priority to European Application No. 17186867.2, filed Aug. 18, 2017, the entire contents of all of which are incorporated by reference herein in their entirety.

FIELD OF THE INVENTION

The invention relates to a patch pump for dispensing a substance such as, for example, insulin, to a user in a metered manner. The pump has a disposable component (also referred to as disposable module) which comprises, for example, consumable elements such as a reservoir for the substance to be dispensed, a cannula, a battery and an adhesive plaster or adhesive surface, and a reusable component (also referred to as reusable module) which contains, for example, a dosing or a dispensing mechanism, for example, in the form of a pump, an energy supply and electrical components such as, for example, a control unit.

BACKGROUND

Certain diseases can be treated by a controlled dispensing of a substance to the body of a patient, wherein the substance dispensing occurs in a controlled manner, for example, continuously or at predetermined times or intervals. For example, diabetes can be treated by the controlled dispensing of insulin in the body of a patient. One possibility of controlled substance dispensing consists of dispensing to a patient by means of an external pump which, for example, is worn by the patient or adhered to the patient's skin, wherein the substance to be dispensed is dispensed from the pump through a catheter introduced into the body of the patient.

From WO 2006/121921 A2, a delivery device consisting of a housing portion and a separable disposable portion is known, wherein the disposable portion can be attached to the patient and contains an infusate, while, in the housing portion, the other components such as, for example, the entire control electronics, batteries and a drive are present.

WO 2009/125398 A2 discloses a fluid dispensing device with a reusable portion with a controller and a drive mechanism and a disposable portion with a reservoir for a fluid, which can be coupled to one another.

U.S. Pat. No. 8,905,972 B2 discloses an infusion pump which can be composed of a baseplate, a cartridge and a reusable portion, wherein an inserter is placed onto the assembled pump in order to pass a cannula through a passage hole of the pump.

SUMMARY OF THE INVENTION

Disposable Module

In the starting state within the disposable housing, a disposable module (also referred to as disposable component) preferably comprises consumable articles such as, for example, a fillable or prefilled reservoir for the substance to be dispensed (for example, insulin), with, for example, a volume of up to 2 mL, a movable or elastic cannula that can be introduced into the patient for dispensing the substance, and, on an outer surface of the housing, an adhesive area or adhesive plaster, in order to be able to adhere the disposable component, for example, to the skin of a patient. Optionally, the disposable module comprises additional components such as, for example, a puncturing or insertion mechanism for the cannula which can be, for example, a soft cannula, or an energy source, for example, a disposable battery or a button cell.

The insertion or injection mechanism for the soft cannula can be formed within the disposable housing as an automatic insertion mechanism which, for example, also stores the energy necessary for the insertion, for example, in the form of a tensioned or compressed spring. The triggering mechanism for the insertion, which, for example, can control or cause the release of the stored insertion energy, for example, can also be provided in the disposable module and, for example, be controlled by the reusable module.

Optionally, a pressure compensation membrane can be provided in the disposable module, for example, in order to compensate for pressure variations which would lead to an undesired discharging.

As mentioned, a battery can be provided in the disposable module, such as, for example, one or more non-chargeable disposable batteries, for example, one or more button cells, which are used for the electric charging of a chargeable storage element for electrical energy or rechargeable batteries in the reusable module. The battery or batteries can be fixedly incorporated in the disposable, and, for example, they can be nondetachably connected to said disposable module, so that the battery cannot be separated from the disposable module or exchanged.

The disposable module or its components are accommodated, for example, in a disposable housing which comprises a connection interface with the disposable module or the reusable module. Here, the lower side of the housing can comprise the adhesive area or the adhesive plaster covered, for example, with a protective film that can be pulled off.

Reusable Module

The reusable module preferably comprises components that are not consumed and that can be used for multiple dispensing processes. Preferably, the reusable module is fitted with the components that, in connection with a disposable module that can be coupled or connected to the reusable module, enable a metered dispensing of a substance. Here, the consumable elements contained in the disposable module, such as, for example, the substance to be dispensed and electrical energy, can be taken up by the reusable module and/or taken up or dispensed by means of the reusable component, which, in the case of a reusable module, is also possible for multiple disposable modules sequentially coupled to the reusable module. For example, the reusable module can receive electrical energy from the disposable module and thus act on the disposable module in such a manner that the substance contained in the disposable module can be dispensed to the user under control by the reusable module from the disposable module, for example, through a cannula. The reusable module should preferably be designed so that it can couple to multiple disposable modules sequentially and in each case receive the transmission of the energy necessary for the operation or the metered dispensing from the disposable module, wherein the substance contained in the disposable module is dispensed either directly from the disposable module by means of a drive or motor present in the reusable module from the disposable module, for example, through a cannula, or alternatively it is transferred to the reusable module and dispensed from it.

The reusable module preferably contains a drive that can be formed, for example, as a motor or an electric motor.

Here, the motor can act directly or indirectly, for example, via a transmission and/or a piston rod and/or a metering mechanism such as, for example, a feed thread, on the reservoir of the substance to be dispensed, for example, on a movable stopper of an ampule, in such a manner that the substance can be dispensed in a controlled or metered manner, for example, when the reusable module is coupled to the disposable module. For example, by an actuation of the motor, a defined substance quantity can be dispensed from the reservoir, for example, continuously at a rate determined by the reusable module and/or at times predetermined by the reusable module.

Preferably, the reusable module comprises electronic components for controlling the drive or motor. Furthermore, optionally, a storage element and/or a data transmission device or radio connecting element can be provided in the reusable module, which, for example, can exchange data with an external control element such as, for example, a mobile telephone, a computer or a pump control app running on a device.

In the same way, the reusable module can, for example, actuate or trigger the insertion device of the disposable module, for example, an energy store (e.g., an energy source such as a spring or a rechargeable energy source) acting on the cannula, or release a force or spring in order to carry out an automatic cannula insertion.

The reusable module has an energy supply such as, for example, a chargeable element or a rechargeable battery, which, for example, can be electrically charged by a battery contained in the disposable module, which is coupled to the reusable module. For example, the energy supply can supply the mentioned electric motor and the optionally present electronic components with current. The chargeable element or rechargeable battery can be incorporated fixedly and, for example, nonexchangeably or else exchangeably in the reusable module.

Optionally, a pressure compensation membrane can be provided.

The reusable module or its components are accommodated, for example, in a reusable module housing that comprises a connection interface with the disposable module.

Connection Interface

The reusable module can be mechanically and/or electrically connected or coupled to the disposable module via an interface. In the same way, for example, a data exchange between the reusable module and the disposable module can be possible, for example, via a radio connection or via the electrical interface.

The mechanical interface or connection or coupling between disposable module and reusable module can be a detachable mechanical connection, for example, in the form of a bayonet closure. Here, the mechanical connection interface can be designed, for example, so that a user has to put the two components, the disposable module and the reusable module, in correct alignment against one another in the area of the connection such as, for example, the bayonet connection, or so that the user turns or has to engage said components into one another and subsequently twists or has to twist them relative to one another by a predetermined angle, until the modules lock into one another. The reusable module and disposable module can, for example, automatically lock or snap with or into one another after a relative rotation has been performed with respect to one another and, optionally, also establish an electrical contact after the locking or snap connection. As a result of the use of a thread-shaped geometry, a bayonet closure or threaded closure can enable the pulling together of the reusable module and the disposable module during the connection or closure of these components and thus implement a play-free connection that can be established by a user with little force exertion.

Preferably, an electrical connection between disposable module and reusable module exists only if they are latched to one another. For example, the electrical contacts on the reusable module and the disposable module can be dimensioned so that they do not yet provide an electrical connection, that is to say, for example, so that there is still a gap between them, when the disposable module and the reusable module have not yet been sufficiently pulled together or, for example, screwed together, to establish a secure connection or locking or latching.

In order to be able to once again release the mechanical connection or latching, a securing or release element such as, for example, a sliding element can be provided, which can be actuated in order to secure or again release the locking or the latching of the components, so that, for example, the components can be twisted relative to one another against the closing direction, in order to release the mechanical coupling or connection, so that the disposable module and the reusable module can be separated from one another. The securing or release element, such as, for example, a sliding element, can be latched electronically, so that the release of the mechanical latching can be controlled electronically, for example, by a control app.

The securing element for securing or locking the connection between the reusable module and the disposable module can be provided, for example, on the reusable module or alternatively on the disposable module. Here, the securing element such as, for example, a slide switch, can be held by a spring in a predetermined position, so that the securing element enables, for example in the starting position, an engagement between the reusable module and the disposable module and prevents an unintended opening of this connection by the pretensioning of the spring. A user has to intentionally move the securing element or a slide switch against the securing force or spring force and, in the case of a simultaneously provided thread connection or bayonet connection, the user also has to perform at the same time a rotation, in order to be able to open the connection between the disposable module and the reusable module.

The mechanical interface between the reusable module and the disposable module can be designed to be play-free. This is advantageous, since the mechanical connection between the reusable module and the disposable module, for example, during the operation of the pump, receives the discharge forces of the syringe pump or of the motor. As a result of a play-free mechanical connection, it can be ensured that the quantity of substance to be dispensed can be precisely controlled and is not influenced incorrectly by a force applied from outside.

Preferably, the interface is water-tight at least in the area of the metering mechanism or discharge mechanism.

The reusable module is preferably produced entirely or at the mechanical or coupling interface with the disposable module from a low-wear material and/or a relatively hard material such as, for example, a hard plastic and/or a metal. The disposable module is preferably produced on the mechanical interface with the reusable module from a relatively soft material that can provide tolerance compensation by plastic deformation and that enables a play-free connection with the reusable module. The remaining portion of the disposable module can also be produced from a hard metal.

The connection can comprise a gasket, made, for example, of a soft component such as silicone, for example, which is, for example, fastened directly on a housing portion. If the gasket is attached to the disposable module, then a high functional reliability can be ensured, since this gasket is replaced by a new gasket at each exchange of the disposable module.

The electronic interface between the reusable module and the disposable module can perform one or more of the following functions:
1. Wake-up of the reusable module electronics from the storage state during the connection of the disposable module
2. Transmission of electrical energy for charging the rechargeable battery from the disposable module which contains, for example, a disposable battery, to the reusable module
3. Verification of the presence of a disposable module on the reusable module
4. Reading and writing of disposable module information, such as, for example, reading out and/or verification of the expiration date of the connected disposable module, type verification (for example, version, reservoir size) of the disposable module by the reusable module or by software of the reusable module, wherein, optionally, as a function thereof, an adjustment of the discharge can be carried out
5. Signal for triggering or releasing the insertion or puncture mechanism of the cannula from the reusable module to the disposable module
6. Transmission of the electrical energy for triggering the insertion or puncture mechanism from the reusable module to the disposable module
7. Verification to determine whether the insertion of the cannula or needle in the disposable module has been performed by the reusable module.

The electronic interface can be formed, for example, by electrical contacts, which is preferably the case when electrical energy is transmitted from the disposable module to the reusable module, for example, for charging a rechargeable battery of the reusable module. Control commands can also be transmitted, for example, via electrical contacts or also wirelessly, for example, by radio.

Cannula

A cannula is a fluidic connection such as, for example, a rigid, non-elastic or elastic tube, needle or a hose, through which a substance or a fluid can be transported. The cannula is preferably in fluidic connection with a reservoir that contains the substance to be dispensed, at least after the insertion, i.e., after the cannula has been pushed out of the pump, that is to say, for example, out of the disposable module housing of the pump, or after the cannula tip has penetrated a patient. Here, according to an embodiment of the present invention, the cannula can also be permanently or continuously in fluidic connection with a reservoir, that is to say, for example, already before the performance of the insertion process. Thus, for example, a fluidic connection of the reservoir to the cannula is not established only during the insertion.

The cannula can be, for example, a hard cannula made of a metal, for example, through which a substance can be conveyed. Preferably, the hard cannula has a pointed front end that is suitable for the insertion, with a passage opening, and which can be stuck, for example, like a known syringe, through the skin and through which a substance can be dispensed.

According to an embodiment, the cannula can be formed as a soft cannula, that is to say it can be produced from a soft and deformable or bendable elastic material which, for example, can be inserted by pricking in a manner which in itself is known, in that, within the soft cannula, an insertion needle or also a hard cannula is provided, which protrudes from the front opening of the soft cannula and which performs the insertion itself, that is to say, for example, which pierces the skin of a patient and which, during the insertion or puncturing process, also moves the soft cannula surrounding the hard cannula, so that the soft cannula as well is inserted or introduced. After the insertion has occurred, the soft cannula can remain in a known manner at the site of the insertion, for example, in that the soft cannula is prevented from being pulled back, or, for example, in that it is latched on the housing, wherein the needle or hard cannula is pulled back out of the soft cannula, so that the needle or hard cannula is no longer inserted.

According to an embodiment, the hard cannula can also remain in a pulled-back state after the insertion in the soft cannula, so that, for example, a substance contained in a reservoir flows through the hard cannula which is, for example, firmly connected or fluidically connected to the reservoir and which, at its front outlet opening, delivers the substance to the soft cannula which surrounds it, and in which the hard cannula has remained after the insertion, so that the substance can be transported through the soft cannula at the insertion site and, for example, through the surface of the skin of a patient, in order to be dispensed at the outlet opening of the soft cannula after the insertion, for example, in a patient.

According to an embodiment example, after the insertion, both the hard cannula and also the soft cannula remain in fluidic connection with the reservoir, wherein, after the insertion has occurred, the hard cannula is moved relative to the soft cannula, that is to say, for example, pulled back in said soft cannula or pulled into said soft cannula.

Alternatively, it is possible that, between the soft cannula and optionally also the hard cannula, a fluidic connection with a reservoir is established only with the insertion or after the insertion has occurred.

After the insertion, that is to say before the introduction of the cannula (hard cannula and/or soft cannula), the injection, that is to say the metered dispensing of a substance through the cannula, can be started.

Aspects of the Invention

According to one aspect, the invention relates to a disposable module that can be coupled to a reusable module, resulting, in the assembled state, in a functioning pump for the metered dispensing of a substance. The disposable module has no drive or motor and, for example, it also has no or no complete control electronics unit, which are provided, for example, exclusively in the reusable module, and it preferably contains, in a disposable module housing, a prefilled or fillable reservoir for receiving or storing the substance, for example, a medically active substance, which is to be dispensed in a metered manner. Moreover, in the housing, a cannula is provided, in particular a soft cannula and/or hard cannula as described above, which is in fluidic connection with the reservoir, at least after being inserted or in a permanent manner. Consequently, the cannula is not added externally with respect to the disposable module, but instead it is already present in the disposable module and, for example, can be shifted or pushed out of the disposable module by means of a suitable insertion mechanism that is also entirely contained in the housing, in order to thus perform an insertion.

Since, according to the invention, the cannula can already be present together with the reservoir in the disposable module housing, the cannula, for example, can be kept sterile with great reliability, since a user cannot touch the cannula before or on the insertion.

Optionally, the complete insertion mechanism can also be provided in the housing, by means of which the cannula can be shifted out of the housing. Alternatively, the insertion mechanism can also lie partially or entirely outside of the housing and, for example, externally, that is to say from outside the housing, provide a force that can be transmitted to the cannula in the disposable module housing in order to perform the insertion. According to an embodiment, the insertion mechanism together with the reservoir and the cannula consisting, for example, of a soft cannula and a hard cannula as described above, is provided in the disposable module housing. The insertion mechanism can be or contain, for example, an energy storage element such as, for example, a tensioned spring or compression spring, which, for example, is retained by a retaining element, so that after the release of the holding element, the energy contained in the energy storage can be transmitted to the cannula, in order to push said cannula out of the disposable housing. For example, after release of the retention connection and release of the compression spring, a compression spring retained by a mechanical element can act on the cannula, that is to say, for example, on the hard cannula and/or soft cannula, in such a manner that, said cannula(s) is/are pushed out of the disposable module housing due to the spring force. The force transmission from an insertion mechanism to the cannula can be configured, for example, mechanically as described in U.S. Pat. No. 8,905,972 B2, wherein, however, for example, a spring element can be arranged, for example, horizontally within the disposable module housing.

Optionally, within the housing, a charge battery or current source, for example, a disposable battery or button cell, can also be provided, which can be used for charging a chargeable electric element or rechargeable battery of the reusable module, when the disposable module is connected or coupled electrically to the reusable module.

By integrating a battery in a disposable module that can be coupled to a reusable module and exchanged after a certain time, it is no longer necessary that a battery on the reusable module has to be exchanged. The reusable module can thus remain unopened in a prefabricated, for example, closed and sealed state, and, from the disposable module, it preferably also receives the supply of electrical energy necessary for dispensing the substance present in the disposable module and delivered by the disposable module. The disposable module can be exchanged with a completely or partially emptied battery and, depending on the application case, with a partially or completely emptied substance reservoir after a duration of use.

The disposable module battery can be a disposable battery, that is to say, for example, a non-rechargeable battery such as, for example, one, two or more button cells, which is, for example, fixedly incorporated in the disposable module, that is to say, for example, fixedly connected to a disposable module housing.

The disposable module can comprise an insertion mechanism for a cannula such as, for example, a soft cannula present in the disposable module. Here, the insertion energy necessary for the insertion can also be stored, for example, in the disposable module, for example, in the form of one or more tensioned springs that is/are secured by a securing element so that the insertion is not yet triggered. The securing element can be released, for example, by a user, by a signal input at a control device that is in the reusable module or in connection with the reusable module, wherein the reusable module transmits the release signal to the disposable module, in order to trigger the automatic insertion mechanism. Here, the disposable module should be coupled to the reusable module and should be attached or adhered at an appropriate site on the patient. Alternatively, the insertion release signal can also be entered directly on the reusable module or also directly on the disposable module.

The disposable module preferably has an adhesive surface that is used for fastening the disposable module to a surface, for example, the skin of a user. The adhesive surface can be covered by a protective film so that, as in the case of a known adhesive plaster, this adhesive surface is only exposed as a result of the removal of the protective film, preferably immediately before the adhering. The base plate of the disposable module can be formed so that the adhesive plaster is fastened or attached only on the disposable module.

According to an additional aspect, the invention relates to a disposable module or to a reusable module that has a drive or motor that can convert electrical energy into mechanical energy, for example, in order to act on a reservoir of the substance to be dispensed of a disposable module connected to the reusable module, so that the substance can be dispensed in a controlled and metered manner. Moreover, the reusable module comprises a chargeable electrical store, for example, a rechargeable battery, which can be charged, for example, by a battery contained in the disposable module, when the disposable module is or will be coupled to the reusable module.

Preferably, the motor or drive of the reusable module drives a piston or a threaded rod that can act on the reservoir of the disposable module in order to dispense a substance from the reservoir in a controlled manner. For example, the piston or the threaded rod can act on a shiftable stopper of the reservoir and slide said stopper, for example, into the reservoir such as, for example, an ampule, in order to displace a substance contained therein and dispense it through a reservoir dispensing opening which, for example, can be a cannula or be connected to a cannula, in order to dispense the substance.

The chargeable electrical energy store element or rechargeable battery can be connected, for example, fixedly to the reusable module, for example, to the reusable module housing, or it can be connected exchangeably to the reusable module.

In the reusable module, additional electric or electronic components can be present, which can preferably be supplied by the energy store element or rechargeable battery with current and, for example, be used for controlling the motor, and which enable a direct or radio communication with an external operating module of a user, such as, for example, a computer or a mobile telephone, so that the user can obtain information on the reusable module and/or disposable module and said information can be displayed for said user, and so that the user can transmit control commands to the reusable module or from said reusable module to the disposable module. The control contained in the reusable module can, for example, actuate the motor contained in the reusable module and it can also, for example, trigger or release the cannula insertion of an automatic insertion mechanism in the disposable module, when the disposable module is connected to the reusable module.

According to an additional aspect, the invention relates to a pump or a dispensing device for dispensing a substance with a reusable module as described above, which is coupled or connected to a disposable module as described above.

According to an additional aspect, the invention relates to an interface between a reusable module as described above and a disposable module as described above, which is configured to be able to transmit electrical energy or a charging current from the disposable module for charging an electrical energy store element or a rechargeable battery in the reusable module. Preferably, an electrical contact consisting of at least two separate lines is provided here.

The interface can also be designed to be able to transmit or exchange data between the reusable module and the disposable module.

Advantageously, the electrical contacts are sealed so that no fluid can reach the interface and preferably also so that fluid cannot reach the electrical components of the disposable module or of the reusable module through the interface.

According to an additional aspect, the invention relates to a method for providing or operating a dispensing device or a pump for a substance, consisting of a reusable module as described above and a disposable module as described above, wherein the disposable module can be or is coupled to the reusable module, and, in the coupled state, electrical energy is transmitted from the disposable module to the reusable module.

BRIEF DESCRIPTION OF THE DRAWINGS

Below, the invention is described in reference to the appended figures which show embodiments of the invention.

DETAILED DESCRIPTION

Figure 1:
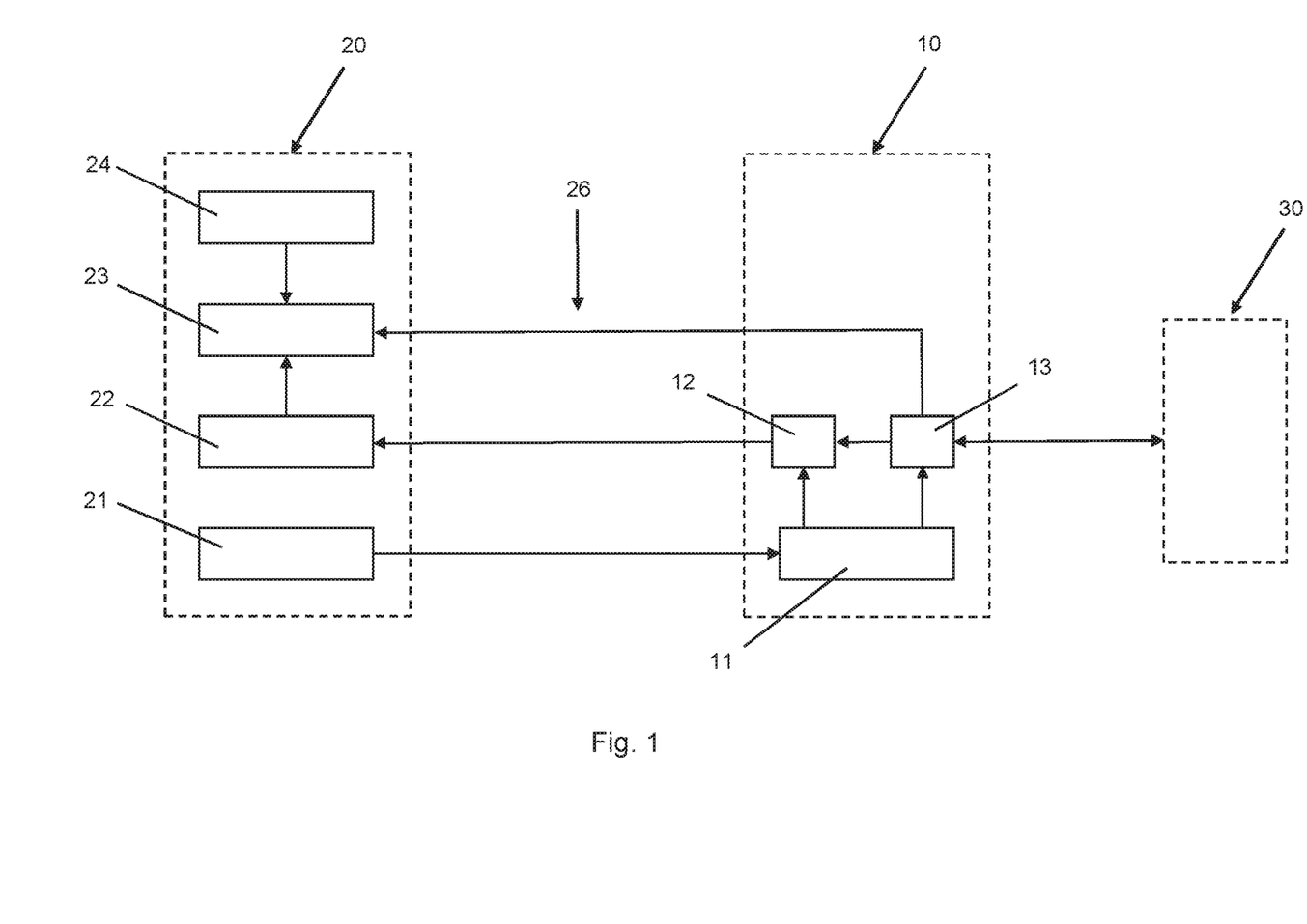
FIG. 1 shows a diagrammatic representation of the components of a pump consisting of a disposable module and a reusable module according to an embodiment.

FIG. 1 shows, in a diagrammatic representation, an embodiment example of a disposable module 20 that comprises a reservoir 22 for a substance to be dispensed, which can be prefilled or designed to be Tillable through a filling opening. The reservoir 22 is already permanently, that is to say without interruption, in fluidic connection with a cannula 23 in the starting state before an insertion, so that a substance can be dispensed through the cannula 23 from the reservoir 22.

The cannula 23 can be pushed or expelled, for example from a disposable module housing, by means of a cannula insertion mechanism 24 powered by an energy source (such as one or more springs) provided in the housing of the disposable module 20, in order to perform an insertion, and the cannula 23 can, for example, be inserted by puncturing through the skin of a user.

In the disposable module 20, that is to say, for example, enclosed by the disposable module housing and/or firmly connected thereto, for example, embedded by casting therein, a battery 21 is provided, for example, in the form of a disposable battery or a button cell.

In the embodiment shown, a reusable module 10 comprises an electrical energy store element in the form of a rechargeable battery 11 which, when the disposable module 20 and the reusable module 10 are electrically connected to one another, can be charged by the battery 21 of the disposable module 20. The rechargeable battery 11 is used for the current supply of the motor 12 contained in the reusable module 10 and for the control 13 (e.g., a microprocessor) that is used for the control of the motor 12 and can exchange data with an external control device 30, for example, via a radio connection. On the external control device 30, for example, software (control app) can be implemented, which enables a user to engage in a contactless interaction with the reusable module 10 and the disposable module 20 coupled thereto.

The motor 12 can act mechanically on the reservoir 22 in order to dispel a substance contained therein if, for example, via the control app running on the external control device 30, corresponding signals have been transmitted to the control 13, and the control 13 accordingly actuates the motor 12.

Figure 2:
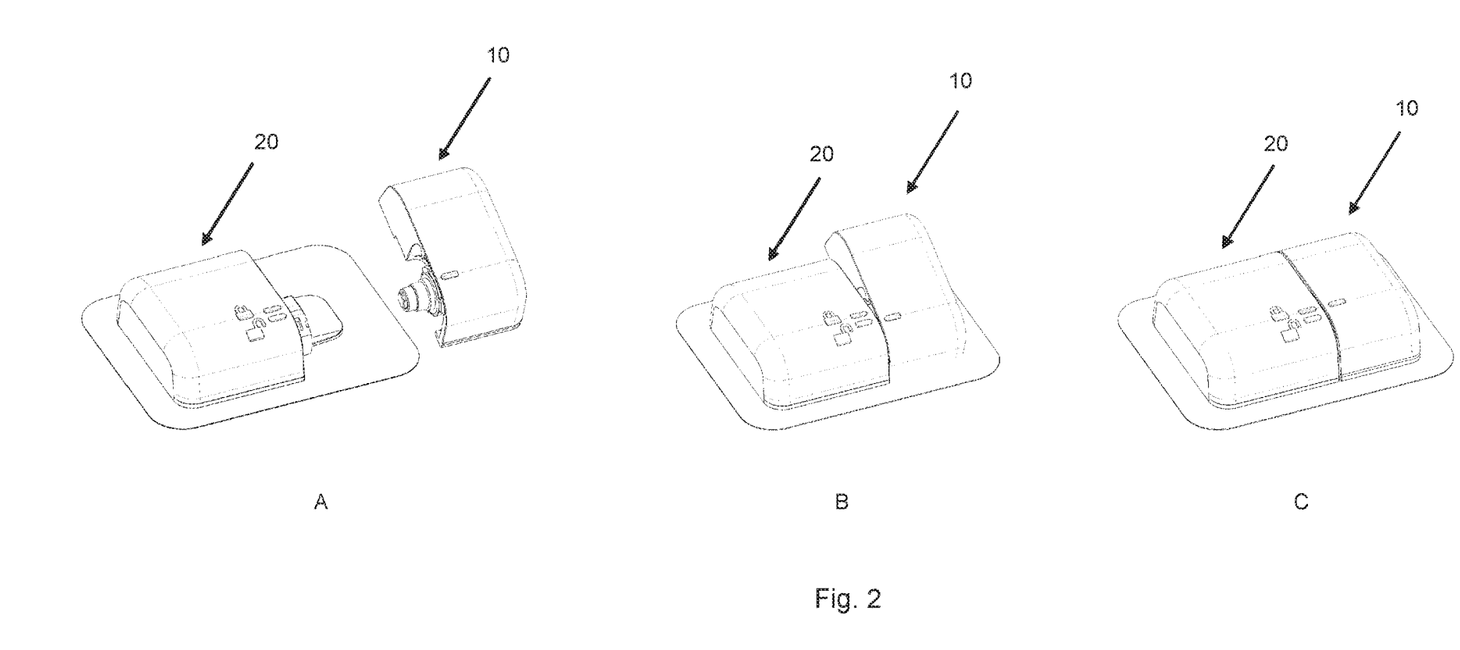
FIG. 2 shows the assembly of a disposable module and a reusable module according to an embodiment.

FIGS. 2A to 2C show the connection of the disposable module 20 to the reusable module 10 in the embodiment example of a bayonet closure. Here, first, as shown in FIG. 2A, components that are present separately, reusable module 10 and disposable module 20, are assembled, as shown in FIG. 2B, and subsequently turned relative to one another for the firm and play-free connection around the bayonet closure, until they are flush in contact with one another, as shown in FIG. 2C.

Figure 3:
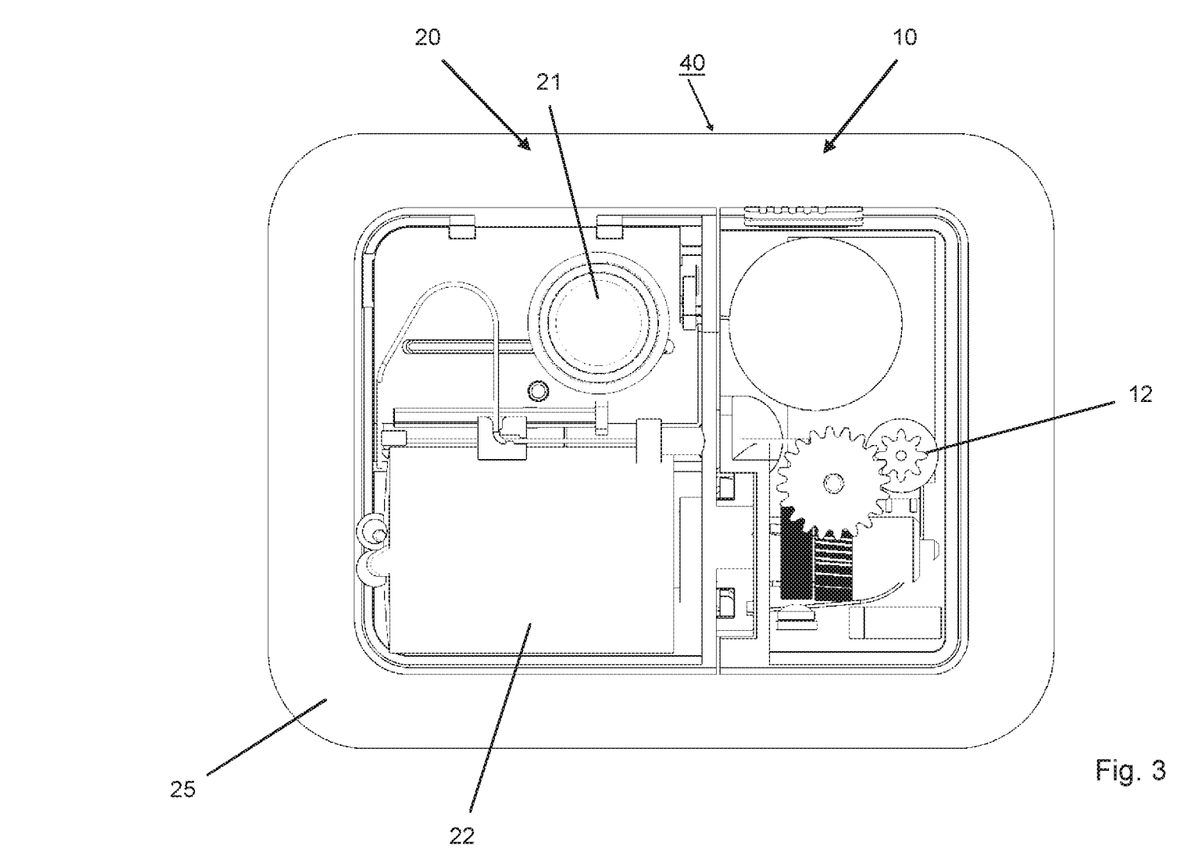
FIG. 3 shows an embodiment of a patch pump consisting of a disposable module and a reusable module.

FIG. 3 shows, in a top view, an embodiment example of a patch pump 40 consisting of disposable module 20 and reusable module 10, with an adhesive plaster element 25, attached to the bottom side of the disposable module 20, with an adhesive surface for adhesion to the assembled pump.

According to an embodiment, the disposable module 20 can be filled before or after the assembly with the reusable module 10. Here, for example, a syringe that is in itself known can be used as a transfer filling aid. For example, the substance to be dispensed, such as, for example, a drug, is filled from a primary packaging means (vial) into the syringe. From the filled syringe, the substance or the drug is dispensed through a filling opening into the reservoir 22 of the disposable module 20.

After the assembly of reusable module 10 and disposable module 20, or after the actuation of the filling process, for example, the filling quantity of the reservoir 22 can be determined. For this purpose, it can be determined, for example, where the stopper of the reservoir 22, which has been shifted by the filling process of the reservoir 22, is located, for example, in that the motor 12 is actuated so that a piston rod is deployed in the direction of the stopper, and it is observed when the piston rod strikes the stopper, in that, for example, the motor current is measured.

The user can apply the patch pump to the skin and trigger the insertion of the needle and subsequently also the insulin delivery.

Figure 4:
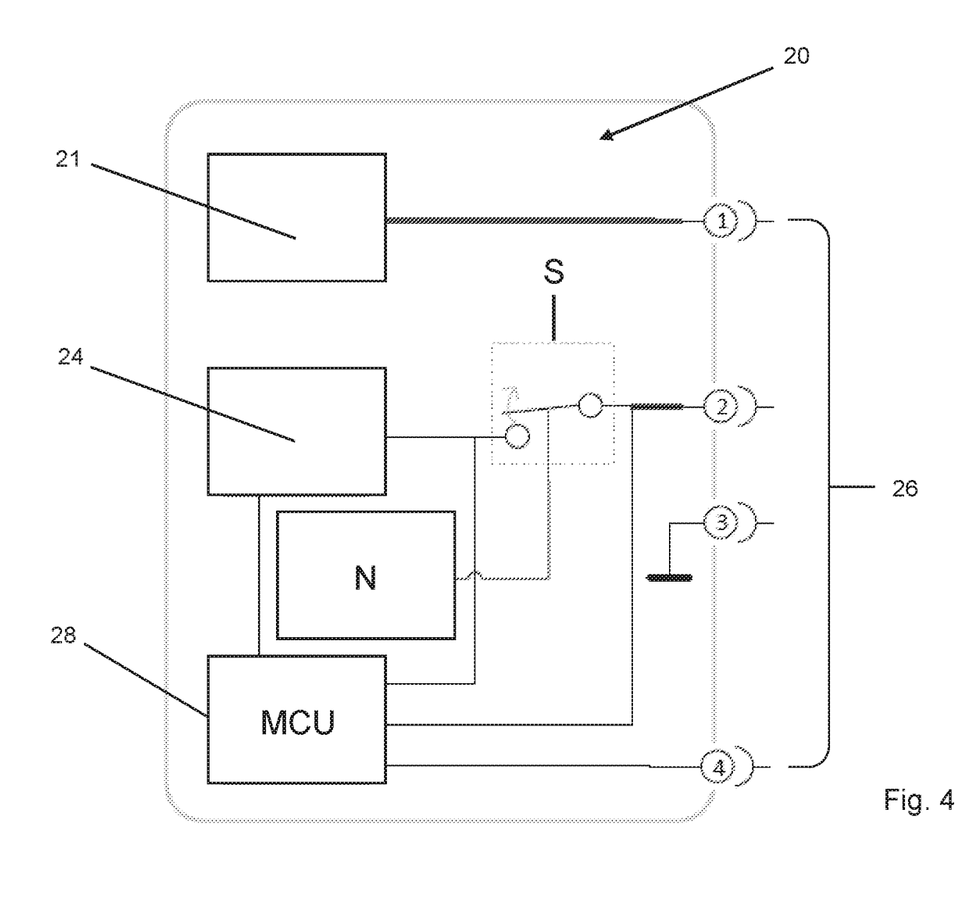
FIG. 4 shows a diagrammatic representation of an embodiment of a disposable module with an interface with the electrical contacting.

FIG. 4 diagrammatically shows an embodiment example of a disposable module 20 and its electrical contacts 1 to 4 at the interface 26 with the reusable module 10.

The electrical contacts are, for example, injection molded in the housing of the disposable module 20. The contacting site of the interface 26 is preferably sealed in the assembled state and thus provides protection against soiling and water. On the reusable module 10, for example, robust contact surfaces can be provided. On the disposable module 20, for example, contact springs can be implemented, which are exchanged with each exchange of the disposable module 20.

As soon as a disposable module 20 is coupled to a reusable module 10, the control 13 (e.g., microprocessor) in the reusable module 10 is started as a result of the applied disposable battery voltage at the connection 1 shown in FIG. 4. The wake-up of the reusable module 10 is also enabled, for example, with a partially discharged battery 21. If a disposable module 20 with completely discharged battery 21 is connected to a reusable module 10, then no wake-up is possible.

The rechargeable battery 11 of the reusable module 10 is charged or discharged via the battery 21 of the disposable module 20. The charging of the rechargeable battery 11 occurs, in the normal case, with as constant as possible a charging current, whereby the capacity that can be removed from the battery 21 is maximized. The charging current is adjusted, for example, to the charging state of the rechargeable battery 11. Via the applied battery voltage, the presence of the disposable module 20 on the reusable module 10 can also be verified.

The disposable module 20 contains a microcontroller MCU 28 that is designed for reading and writing information on the disposable module 20, such as, for example, version, status of the insertion mechanism 24, reservoir size or expiration date of the substance contained in the reservoir 22. The microcontroller MCU 28 can communicate via the connection 2 or 4 with the reusable module 10 coupled to the interface.

Optionally, a disposable module 20 can be invalidated at any time, if, for example, one or more filling status detections have already been carried out, or, for example, only after the insertion mechanism 24 has been triggered. If an invalidated disposable module 20 is detected by a reusable module 10, then it is rejected, i.e., the reusable module 10 does not make available any dispensing functions, such as, for example, the operating of the motor 12, to the disposable module 20 which has been determined to be invalidated.

The signal for triggering the cannula or needle insertion mechanism 24 can be transmitted to the MCU 28 via a communication interface, for example, at connection 4, which can control the needle insertion mechanism 24.

The battery 21 in the disposable module can optionally be designed to deliver the energy for triggering the needle insertion mechanism 24. This energy can be delivered, for example, via the connection 2 of the rechargeable battery 11 of the reusable module 10.

In the storage state, the switch S for supplying the needle insertion mechanism 24 is closed. During the insertion of the needle or cannula 23, the switch S, which can be switched with the change of the needle position N and which is connected or mechanically coupled to the cannula, is opened. Based on the voltage measurement between the needle insertion mechanism 24 and the switch S, on the one hand, the voltage at the connection 2 before the triggering of the needle or cannula 23 can be verified, and, on the other hand, the status of the switch S can be determined. If the switch S is closed, a voltage drop occurs when the needle or cannula insertion mechanism 24 is switched on. In the open state, no voltage can be measured. The MCU 28 stores the status, and the reusable module 10 can read out the status at any time via the connection 4.

Figure 5:
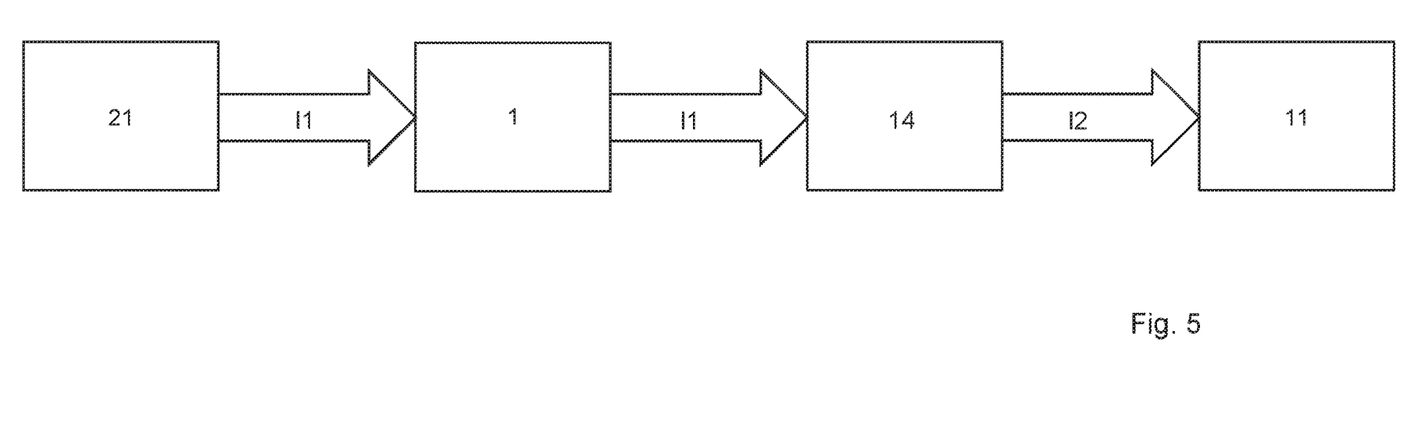
FIG. 5 shows the energy supply design according to an embodiment of the invention.

FIG. 5 diagrammatically shows the energy supply design of the pump, which shows that the operation of the electronics unit, such as, for example, the control 13 of the reusable module 10, can be ensured by the rechargeable battery 11 in the reusable module 10. The battery 21 in the disposable module 20 is used for charging or supplementary charging of the rechargeable battery 11 of the reusable module 10 with the charging current I1. Here, with a charging electronics unit 14, for example, a voltage adaptation or an automatic charging system can be implemented. For example, depending on the type of operation of the charging electronics unit 14, the charging current I1 delivered by the battery 21 can be greater than, identical to or smaller than the charging current I2 provided for charging the rechargeable battery 11. Thus, all the components with high energy consumption, such as, for example, the motor 12 or the drive for the insulin conveyance, an optionally provided buzzer or signaling device, or the triggering of the cannula insertion mechanism 24, can be supplied with electrical energy by the rechargeable battery 11 of the reusable module 10. The battery 21 of the disposable module 20 can be discharged continuously and in a low-loss manner in order to charge the rechargeable battery 11.

If the rechargeable battery 11 is insufficiently charged, for example, for a scheduled therapy, the rechargeable battery 11 is first additionally charged by a quick charging. If, after the minimum charging state of the rechargeable battery 11 has been reached, the battery 21 is not sufficiently charged to supply the desired reservoir quantity of the connected disposable module 20, an exchange of the disposable module 20 can be necessary.

Preferably, the capacity of the battery 21 is greater than the capacity necessary for the predetermined therapy duration of 3 days, for example, and a maximum filling quantity of the reservoir 22. Thereby, the charging state of the rechargeable battery 11 can be increased with each disposable module 20 or each new battery 21.

For example, in the case of failure of the rechargeable battery 11 in the reusable module 10, the battery 21 in the disposable module 20 can be used as an energy source in order to warn the user and, for example, to provide the energy for the warning via a smartphone 30.

Pump Switching Functionality

In connection with the above-described pump, or in general when at least two pumps are used, an exchange or continuation function can be integrated in the control or communication of the pumps in order to support the user during the seamless switching between two pumps.

In the process, while one pump is still active, a second pump, for example, can be filled, activated and applied on the body. If the first pump is empty, this is detected by the first pump, and all the relevant operating parameters such as, for example, current basal rates, boluses and optionally other settings of the most recently still active first pump are transmitted to the new second pump, and the signal is given to said second pump to continue to the extent possible a seamless or interruption-free substance dispensing based on the transmitted data.

Thus, for example, a substance contained in a pump can be used up practically completely, and a discrete switch from one pump to another pump can be enabled, without the user having to intervene, in order to initiate the functional transition from one pump to the other pump.

What is claimed is:
1. A patch pump comprising:
   a disposable module comprising a housing, wherein the housing comprises:
      a reservoir for containing a substance to be dispensed;
      at least one extensible cannula, which is fluidically connected to the reservoir either after being inserted or in a permanent manner;

a cannula insertion mechanism comprising an energy source to drive the at least one cannula in an insertion procedure or to move the at least one cannula out of the housing; and at least one battery; and a reusable module comprising:

a mechanical interface and an electrical interface configured to form a connection with the disposable module; and at least one chargeable electrical energy store or battery, wherein the disposable module can be coupled to the reusable module for dispensing the substance to a user in a metered manner, and wherein the reusable module is configured to be supplied with electric power from multiple interacting energy sources such that the reusable module is supplied with electric power from the chargeable electrical energy store or battery in the reusable module when said at least one chargeable electrical energy store or battery is properly operating, and when the disposable module is coupled to the reusable module, the reusable module is configured to be supplied with electric power from the at least one battery in the disposable module when said at least one chargeable electrical energy store or battery is not properly operating.

2. The patch pump of claim 1, wherein the electrical interface comprises electrical contacts for transmitting electrical energy from the at least one battery in the disposable module to the chargeable electrical energy store or battery in the reusable module for charging.

3. The patch pump of claim 1, wherein the cannula insertion mechanism is configured to automatically or independently push the at least one cannula out of the disposable module and/or to automatically or independently perform the insertion procedure of the at least one cannula in a user.

4. The patch pump of claim 1, wherein when the disposable module is coupled to the reusable module, the at least one chargeable electrical energy store or battery is configured to be charged with electric energy from the at least one battery in the disposable module when said at least one chargeable electrical energy store or battery is properly operating such that the reusable module is supplied with the electric power from the at least one chargeable electrical energy store or battery.

5. The patch pump of claim 1, wherein the at least one battery of the disposable module is fixedly or detachably connected to the disposable module.

6. The patch pump of claim 1, wherein the at least one battery of the disposable module comprises one or more disposable batteries or button cells.

7. The patch pump of claim 1, wherein the reusable module further comprises:

a drive means and a control means configured to be supplied with electrical energy at least from the chargeable electrical energy store or battery; and a mechanical interface and/or an electrical interface configured to form a connection between the disposable module and the reusable module, in order to trigger the cannula insertion mechanism in the insertion procedure or to move the at least one cannula out of the housing.

8. The patch pump of claim 1, wherein the at least one cannula is a hard cannula and/or a soft cannula.

9. The patch pump of claim 1, wherein the chargeable electrical energy store or battery is a rechargeable battery fixedly or exchangeably connected to the reusable module.

10. The patch pump of claim 7, wherein the control means in the reusable module communicates wirelessly with an external control device for the exchange of control signals.

11. The patch pump of claim 1, wherein an energy quantity contained in the battery of the disposable module is greater than an energy quantity that is necessary for completely dispensing the substance contained in the reservoir of the disposable module.

12. The patch pump of claim 1, further comprising a securing and release element for securing the disposable module and the reusable module when coupled.

13. A method for operating a pump comprising:

coupling a disposable module to a reusable module in order to form a pump for dispensing a substance to a user in a metered manner in a coupled state, the disposable module comprising a housing that encases the following components:

a reservoir for receiving the substance to be dispensed; and at least one extensible cannula, which is fluidically connected to the reservoir either after being inserted or in a permanent manner, and the reusable module comprising:

a chargeable energy store element;

a drive means and a control means that can be supplied with electrical energy by the chargeable energy store element; and a mechanical interface and/or an electrical interface forming a connection between the disposable module and reusable module, in order to trigger a cannula insertion mechanism, wherein a battery of the disposable module is coupled to the chargeable energy store element of the reusable module and charges it, and wherein, in the case of a functioning chargeable energy store element, the energy supplied for the reusable module is provided by said chargeable energy store element, and, in the case of non-functioning chargeable energy store element, it is provided by the disposable module or its battery.

14. The method according to claim 13, wherein an energy quantity contained in the battery of the disposable module is greater than the energy quantity that is necessary for completely dispensing the substance contained in the reservoir of the disposable module.

15. The method according to claim 13, wherein a cannula insertion mechanism drives the at least one cannula for the insertion or moves it out of the housing.

16. The method according to claim 15, wherein the cannula insertion mechanism automatically or independently pushes the at least one cannula out of the disposable module and/or automatically or independently performs an insertion procedure of the at least one cannula in a user.

17. The method according to claim 13, further comprising securing the coupled disposable module and reusable module with a securing and release element.

18. A method for operating a patch pump, comprising:

charging a chargeable energy store element in a reusable module with electric energy from a battery in a disposable module, wherein the reusable module comprises a mechanical interface and an electrical interface configured to form a connection with the disposable module, and wherein the disposable module houses the battery, a reservoir for containing a substance to be dispensed, at least one extensible cannula for dispensing the substance, and a cannula insertion mechanism comprising an energy source to drive the at least one cannula in an insertion procedure or to move the at least one cannula out of the housing;

supplying the reusable module with electric power from the chargeable energy store element in the reusable module while said chargeable energy store element is properly operating; and supplying the reusable module with electric power from the battery in the disposable module if the chargeable energy store element in the reusable module is not properly operating.

19. The method according to claim 18, further comprising the step of driving the at least one cannula in the insertion procedure or for moving the at least one cannula out of the housing.

20. The method according to claim 18, further comprising the step of automatically or independently pushing the at least one cannula out of the disposable module and/or of automatically or independently performing the insertion procedure of the at least one cannula into a user.

* * * * *

UNITED STATES PATENT AND TRADEMARK OFFICE
CERTIFICATE OF CORRECTION

| | |
|---|---|
| PATENT NO. | : 11,406,754 B2 |
| APPLICATION NO. | : 16/693717 |
| DATED | : August 9, 2022 |
| INVENTOR(S) | : Ursina Streit et al. |

It is certified that error appears in the above-identified patent and that said Letters Patent is hereby corrected as shown below:

In the Specification

In Column 9, Line 50 delete ""Tillable"" and insert --fillable--

Signed and Sealed this
Eleventh Day of October, 2022

Katherine Kelly Vidal
*Director of the United States Patent and Trademark Office*